(12) United States Patent
Studer et al.

(10) Patent No.: US 7,166,131 B2
(45) Date of Patent: Jan. 23, 2007

(54) INTERVERTEBRAL DISK PROSTHESIS OR ARTIFICIAL VERTEBRA

(75) Inventors: Armin Studer, Steinhausen (CH); Jason Trachsel, Ipsach (CH); Martin Wymann, Liebefeld (CH)

(73) Assignee: Synthes (USA), West Chester, PA (US)

( * ) Notice: Subject to any disclaimer, the term of this patent is extended or adjusted under 35 U.S.C. 154(b) by 90 days.

(21) Appl. No.: 10/532,908

(22) PCT Filed: Oct. 28, 2002

(86) PCT No.: PCT/CH02/00582

§ 371 (c)(1), (2), (4) Date: Apr. 27, 2005

(87) PCT Pub. No.: WO2004/037131

PCT Pub. Date: May 6, 2004

(65) Prior Publication Data

US 2006/0052871 A1   Mar. 9, 2006

(51) Int. Cl.
*A61F 2/44* (2006.01)

(52) U.S. Cl. ................... 623/17.16; 623/17.11

(58) Field of Classification Search ... 623/17.11–17.16
See application file for complete search history.

(56) References Cited

U.S. PATENT DOCUMENTS

| 4,932,975 A | 6/1990 | Main et al. |
| 5,002,576 A | 3/1991 | Fuhrmann et al. |
| 6,395,032 B1 | 5/2002 | Gauchet |
| 6,582,468 B1 | 6/2003 | Gauchet |
| 6,692,495 B1 * | 2/2004 | Zacouto ................ 606/61 |

FOREIGN PATENT DOCUMENTS

DE   9000094.3   1/1991

* cited by examiner

*Primary Examiner*—Tom Barrett
(74) *Attorney, Agent, or Firm*—Jones Day

(57) ABSTRACT

An intervertebral disk prosthesis having an essentially hollow cylindrical base element (1) which is provided with a casing (2) that is embodied as a bellows, a top end (3), and a bottom end (4), and a central longitudinal axis (5). The base element also includes an upper apposition plate (6), which is disposed perpendicular to the longitudinal axis (5) at the top end (3) of the base element (1) and rests on the base plate of the vertebra, and a lower apposition plate (7), which is arranged perpendicular to the longitudinal axis (5) at the bottom end (4) of the base element (1) and leans on the cover plate of a vertebra. The casing (2) serves a spring element having a defined spring rate.

25 Claims, 3 Drawing Sheets

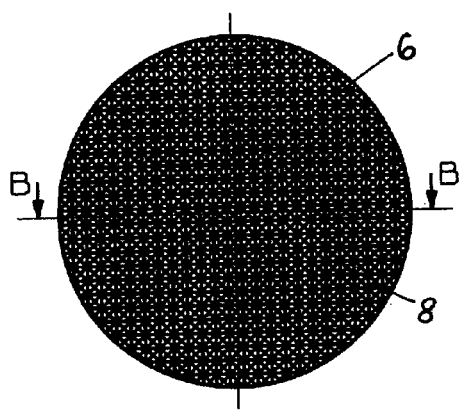
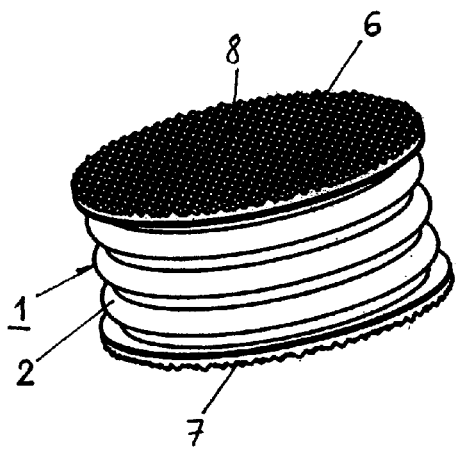
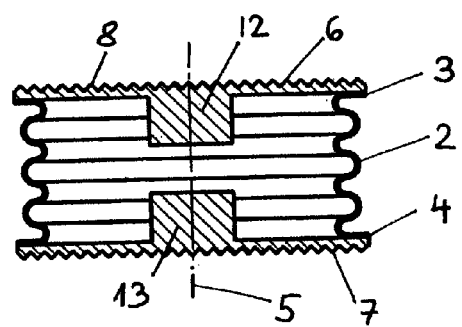
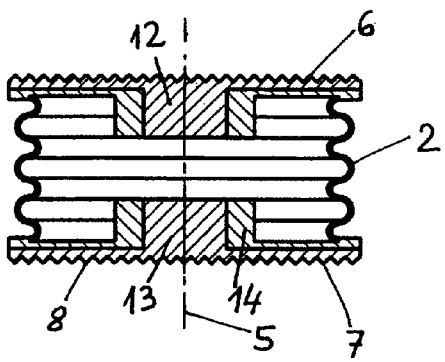
Fig. 2
Fig. 1
Fig. 3
Fig. 4

INTERVERTEBRAL DISK PROSTHESIS OR ARTIFICIAL VERTEBRA

BACKGROUND OF THE INVENTION

The invention concerns an intervertebral disk prosthesis or an artificial vertebral body.

From U.S. Pat. No. 4,932,975 Main et al. a vertebra prosthesis is known, that comprises an expandable bellows as the basic body. The bellows is made from a flexible material, that allows an expansion of the bellows. However, in the case of this bellows basically one deals with a passive element, that through an opening can be filled with a fluid, while the bellows passively stretches. Thus in the case of this known device it lacks an active elastic element that could flexibly absorb the loads. In addition, a further disadvantage of this known vertebral body prosthesis is that subsequently it has to be filled with a fluid, e.g. a methacrylate (in particular methyl methacrylate MMA), representing considerable risks.

From WO 00/35383 Dimso, an intervertebral disk prosthesis of the generic type is known. This known intervertebral disk prosthesis comprises a compressible body between two plates, said body is enveloped by a bellows-like jacket. The disadvantage of this known intervertebral disk prosthesis is its low stiffness.

BRIEF SUMMARY OF THE INVENTION

This is where the invention wants to provide remedy. The object of the invention is to produce an intervertebral disk prosthesis or an artificial vertebral body, that has axially dampening components, so that both the translation, rotation and the angulation can be absorbed and transmitted in a defined manner.

The objective set by the invention is achieved with an intervertebral disk prosthesis or an artificial vertebral body, having the features of the disclosed embodiments.

The advantages essentially achieved by the invention are that by virtue of the intervertebral disk prosthesis or the artificial vertebral body the function and the task of an intervertebral disk or of a natural vertebral body can be reproduced as close as possible.

Further advantageous configurations of the invention are disclosed herein.

The comments regarding each embodiment are made in most cases based on an intervertebral disk prosthesis; all embodiments refer, however, also to a possible construction as an artificial vertebral body.

The specific spring rate of the spring element should be preferably at least 50 N/mm, preferably at least 100 N/mm. The spring rate is, however, preferably 150 N/mm, preferably at least 400 N/mm. The spring rate should be limited also upwards and be maximum 800 N/mm, preferably maximum 2000 N/mm. The spring rate is typically 600 N/mm.

In the case of a load of 1000 N the spring travel of the spring element should be in the range of 1–2 mm, preferably in the range of 1.3–1.7 mm. The spring travel under this load is typically 1.5 mm.

According to an embodiment of the invention the spring element is constructed both as a tension spring and as a compression spring.

The number of folds of the jacket, constructed as bellows, is preferably in the range of 3–10, preferably 4–5. This number is advantageous both for the production technology and the desired stretching of the material used.

According to an embodiment of the invention the jacket comprises a plurality of single layers. Thus the stiffness of the bellows can be controlled arbitrarily within certain limits.

In the case of a special embodiment the single layers are spaced from one another. By virtue of this construction various bellows can be combined with one another, that can accept various loads, e.g. an external bellows for the angulation, translation, rotation and dampening of a load, for example, 800 N and an internal bellows to accept loads of approx. 2500 N, so that the external bellows will be protected.

In the case of another special embodiment the single layers abut against one another without intermediate layers. Thus the stiffness can be increased.

In the case of another embodiment the jacket comprises a plurality of bellows inserted into one another.

The jacket may also have slots, that should extend basically parallel to the longitudinal axis. By virtue of this the rotational stiffness of the bellows will be reduced.

The rotational stiffness of the jacket should be so chosen, that it would allow 1°–3° rotation of the jacket, preferably 1.5°–2.5°.

When using an axial force of 800 N, the axial stroke of the jacket should be preferably in the range of 1.0–2.5 mm, preferably in the range of 1.30–1.75 mm.

According to an embodiment of the invention both apposition plates are fastened on the top and bottom ends of the basic body axially firmly but enabling rotation.

In the case of an alternative embodiment both apposition plates are axially fastened on the top and bottom ends of the basic body and their rotation about the longitudinal axis is limited, preferably to an angular range of maximum 5°.

In the case of another alternative embodiment both apposition plates are fastened on the top and bottom ends of the basic body axially firmly and unable to rotate.

In the case of a special embodiment the rotational stiffness of the jacket constructed as bellows is so chosen, that both apposition plates can be rotated relative one another about the longitudinal axis by an angle of 1°–5°, preferably 2°–3°.

In the case of a further embodiment both apposition plates can be tilted from the plane that is orthogonal to the longitudinal axis by an angle of 4°–8°, preferably 5°–7°.

In the case of a particular embodiment of the invention the hollow-cylindrical basic body is filled at least partially with a solid body, preferably a synthetic material, acting as a dampening element. By virtue of this construction the stiffness will be increased and a better absorption of greater shock loads, e.g. 2500 N, will result.

The jacket of the intervertebral disk prosthesis can be made from a metal, e.g. titanium or a metal alloy, preferably based on titanium. The material of the jacket should preferably have a minimum stretch limit of 30%, preferably a minimum of 38%. The jacket can be made, however, also from a synthetic material, preferably an elastomer.

In the case of a special embodiment of the invention the jacket is made from a packet of cup springs.

BRIEF DESCRIPTION OF THE DRAWINGS

The invention and developments are explained in detail in the following based on the partly schematic illustrations of several embodiments.

They show in:

FIG. 1—a perspective view of an intervertebral disk prosthesis,

FIG. 2—a top view on the intervertebral disk prosthesis according to FIG. 1,

FIG. 3—a longitudinal section along line B—B of FIG. 2,

FIG. 4—a version of the intervertebral disk prosthesis according to FIG. 1, longitudinally sectioned, FIG. 5—a perspective view on an intervertebral disk prosthesis with a central bore, FIG. 6—a top view on an intervertebral disk prosthesis according to FIG. 5, FIG. 7—a longitudinal section along line B—B of FIG. 6, and FIG. 8—a perspective view of a partially sectioned intervertebral disk prosthesis with two bellows, inserted into one another.

DETAILED DESCRIPTION OF THE INVENTION

Figure 6:
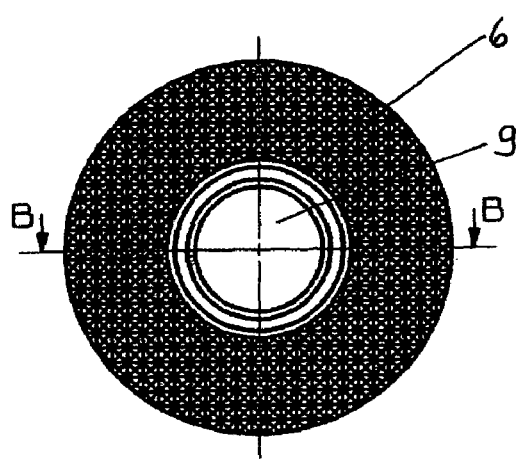

The intervertebral disk prosthesis, illustrated in FIGS. 1–3, essentially comprises a hollow-cylindrical basic body 1 with a jacket 2 constructed as a bellows, a top end 3, a bottom end 4 and a central longitudinal axis 5. On the top end 3 of the basic body 1 a top apposition plate 6 is provided transversely to the longitudinal axis 5, that is intended as a support for the base plate of a vertebral body. On the bottom end 4 of the basic body 1 a bottom apposition plate 7 is provided transversely to the longitudinal axis 5, that can be placed on the cover plate of a vertebral body.

Both apposition plates 6, 7 have an outwardly structured surface 8, that is made up from a plurality of pyramid-shaped teeth, so that to achieve a better contact with the base and cover plates of the adjacent vertebral bodies. The structured surface 8 can be also realised in the form of etching the surface or in the form of surface structures promoting the adherence of the bone tissue.

The jacket 2, constructed as an external bellows, has altogether three to six folds (waves).

The height of the intervertebral disk prosthesis is 5–15 mm, depending from the embodiment, the diameter is in the range of 10–35 mm and the thickness of the jacket is approx. 0.1 mm.

Both apposition plates 6, 7 have inward facing axial spigots 12 and 13, that can be constructed as dampening elements.

In the case of the version illustrated in FIG. 4 both apposition plates 6,7 with the inward facing axial spigots 12 and 13 as bearing spigots are rotatably mounted in a housing 14, while the rotation can be limited by stops (not illustrated).

Figure 5:
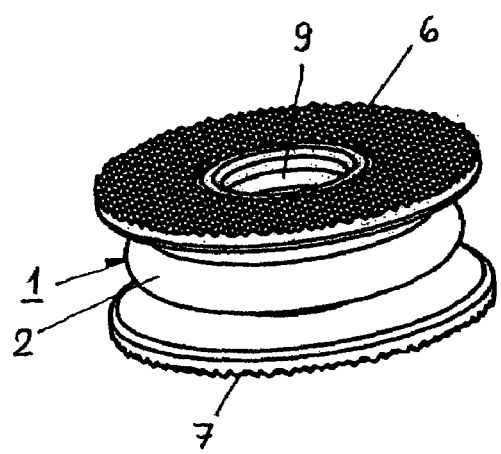
Figure 7:
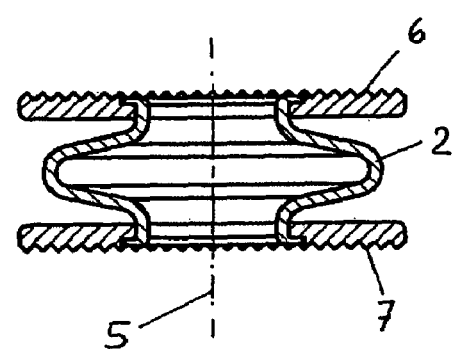

The embodiment of an intervertebral disk prosthesis, shown in FIGS. 5–7, is similarly constructed to those according to FIGS. 1–3. The difference is that both apposition surfaces 6, 7 are constructed as annuluses, so that a bore 9, axially passing through it, will result. A further difference is that in the case of this embodiment the jacket 2, constructed as bellows, has only one fold (wave).

Figure 8:
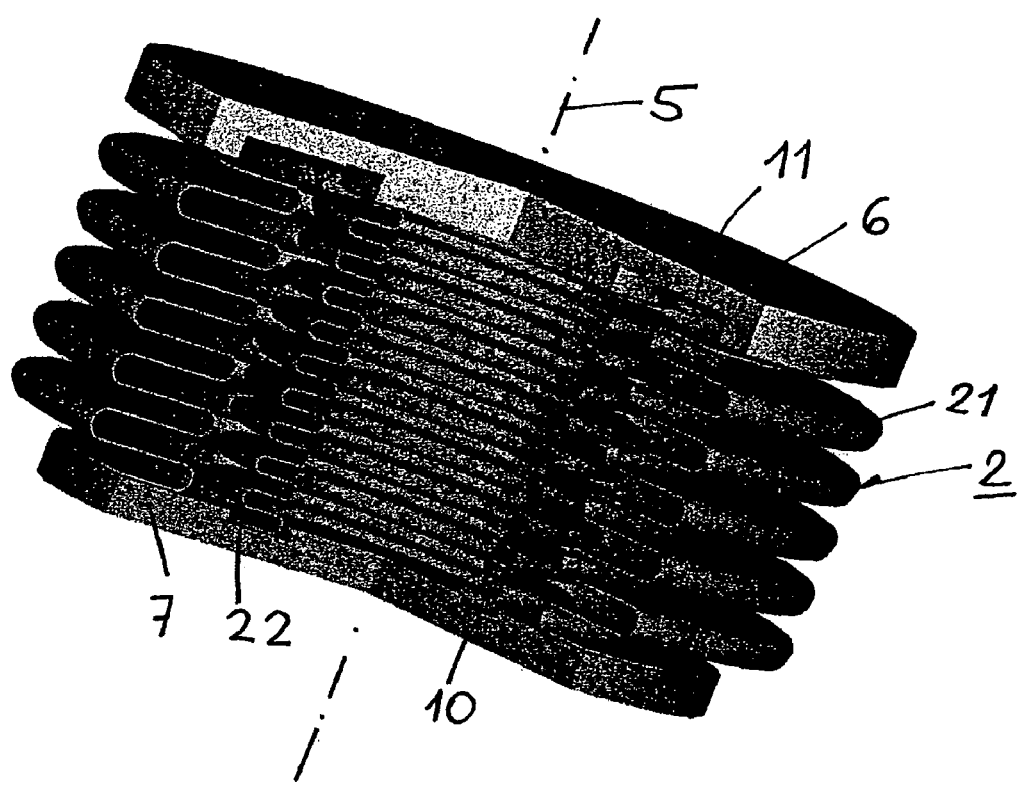

FIG. 8 shows particularly graphically the operation of the intervertebral disk prosthesis. In the case of this embodiment the jacket 2 comprises an external bellows 21 and an internal bellows 22. The external bellows 21 has five folds and the internal bellows 22 has nine folds. The external bellows 21 is fastened on the top apposition plate 6 and the internal bellows 22 on the bottom apposition plate 7. Depending on the material the bellows can be welded to the apposition plates 5, 6, caulked or pressed into them. In the embodiment illustrated both bellows 21, 22 are let into annular grooves 10 and 11, that are provided on the inside of both apposition plates 6, 7. As FIG. 8 illustrates, the two apposition plates 5, 6, that can be fastened on a bellows 21, 22 each, can be fitted together to form a box. Consequently the two apposition plates 5, 6 can rotate relative one another. By virtue of a stop (not illustrated) the rotation can be limited to a predetermined value, e.g. 2°–3°.

The invention claimed is:

1. An intervertebral disk prosthesis or an artificial vertebral body, comprising:
    A) an essentially hollow-cylindrical basic body (1) with a jacket (2) constructed as a bellows, a top end (3), a bottom end (4) and a central longitudinal axis (5),
    B) a top apposition plate (6), provided transversely to the central longitudinal axis (5) on the top end (3) of the basic body (1), said top apposition plate (6) serving as a support for a base plate of a vertebral body, and
    C) a bottom apposition plate (7), provided transversely to the central longitudinal axis (5) on the bottom end (4) of the basic body 1, said bottom apposition plate (7) being adapted for placement on a cover plate of a vertebral body, and
    D) the jacket (2), constructed as a bellows, is constructed as a spring element with a specific spring rate, wherein
    E) the jacket (2) comprises a plurality of bellows inserted into one another.

2. The intervertebral disk prosthesis or artificial vertebral body according to claim 1, wherein the specific spring rate is at least 100 N/mm.

3. The intervertebral disk prosthesis or artificial vertebral body according to claim 2, wherein the spring rate is at least 400 N/mm.

4. The intervertebral disk prosthesis or artificial vertebral body according to claim 1, wherein the spring rate is less than 2000 N/mm.

5. The intervertebral disk prosthesis or artificial vertebral body according to claim 1, wherein, under a load of 1000 N, a spring travel of the spring element is between about 1–2 mm.

6. The intervertebral disk prosthesis or artificial vertebral body according to claim 1, wherein the spring element is both a tensile spring and a compression spring.

7. The intervertebral disk prosthesis or artificial vertebral body according to claim 1, wherein a number of folds of the jacket (2) is between about 3–10.

8. The intervertebral disk prosthesis or artificial vertebral body according to claim 7, wherein the number of folds of the jacket (2) is between about 4–5.

9. The intervertebral disk prosthesis or artificial vertebral body according to claim 1, wherein the jacket (2) comprises a plurality of single layers.

10. The intervertebral disk prosthesis or artificial vertebral body according to claim 9, wherein the single layers of the jacket (2) are spaced from one another.

11. The intervertebral disk prosthesis or artificial vertebral body according to claim 9, wherein the single layers of the jacket (2) abut against one another without intermediate layers.

12. The intervertebral disk prosthesis or artificial vertebral body according to claim 1, wherein the jacket has slots that extend essentially parallel to the central longitudinal axis (5).

13. The intervertebral disk prosthesis or artificial vertebral body according to claim 1, wherein rotational stiffness of the jacket (2) allows a 1°–3° rotation of the jacket.

14. The intervertebral disk prosthesis or an artificial vertebral body according to claim 1, wherein, when an axial force of 800 N is applied, an axial stroke of the jacket is between about 1.0–2.5 mm.

15. The intervertebral disk prosthesis or an artificial vertebral body according to claim 1, wherein the top and bottom apposition plates (6, 7) are firmly axially fastened on the top and bottom ends (3, 4) of the basic body (1), respectively, but so as to enable rotation.

16. The intervertebral disk prosthesis or artificial vertebral body according to claim 1, wherein the top and bottom apposition plates (6, 7) are axially fastened on the top and bottom ends (3, 4) of the basic body (1), respectively, such that rotation of the top and bottom apposition plates about the central longitudinal axis (5) is limited to an angular range of no more than about 5°.

17. The intervertebral disk prosthesis or artificial vertebral body according to claim 1, wherein the top and bottom apposition plates (6, 7) are firmly axially fastened on the top and bottom ends (3, 4) of the basic body (1), respectively, so as to prevent rotation of the top and bottom apposition plates.

18. The intervertebral disk prosthesis or artificial vertebral body according to claim 17, wherein rotational stiffness of the jacket (2) constructed as bellows is so chosen, that the top and bottom apposition plates (6, 7) can rotate relative one another about the central longitudinal axis (5) by an angle of between about 1°–5°.

19. The intervertebral disk prosthesis or artificial vertebral body according to any claim 1, wherein the top and bottom apposition plates (6, 7) can be tilted from a plane that is orthogonal to the central longitudinal axis (5) by an angle of between about 4°–8°.

20. The intervertebral disk prosthesis or artificial vertebral body according to claim 1, wherein the hollow-cylindrical basic body (1) is filled at least partially with a solid body that acts as a dampening element.

21. The intervertebral disk prosthesis or artificial vertebral body according to claim 20, wherein the solid body is formed from a synthetic material.

22. The intervertebral disk prosthesis or artificial vertebral body according to claim 1, wherein the jacket (2) is made from a metal or a metal alloy.

23. The intervertebral disk prosthesis or artificial vertebral body according to claim 1, wherein the jacket (2) is formed from a material having a minimum stretch limit of about 30%.

24. The intervertebral disk prosthesis or artificial vertebral body according to claim 1, wherein the jacket (2) is made from a synthetic material.

25. The intervertebral disk prosthesis or artificial vertebral body according to claim 1, wherein the jacket (2) is made from a packet of cup springs.

* * * * *